United States Patent [19]

Herman et al.

[11] 4,151,142
[45] * Apr. 24, 1979

[54] WET ADHESION EMULSIONS OF POLYMER RESINS SYSTEMS EMPLOYED IN WATER-BASED PAINT AND COATING COMPOSITIONS COMPRISING AS A COMPONENT THEREOF MONOMER CONTAINING AN ETHYLENIC DOUBLE BOND AND A UREIDO GROUP POLYMERIZED THEREIN

[75] Inventors: Frederick L. Herman, Allentown; Dale D. Dixon, Kutztown, both of Pa.

[73] Assignee: Air Products and Chemicals, Inc., Allentown, Pa.

[*] Notice: The portion of the term of this patent subsequent to Sep. 5, 1995, has been disclaimed.

[21] Appl. No.: 873,813

[22] Filed: Jan. 31, 1978

Related U.S. Application Data

[63] Continuation-in-part of Ser. No. 709,677, Jul. 29, 1976, Pat. No. 4,111,877.

[51] Int. Cl.² ............................................. C08L 35/00
[52] U.S. Cl. ........................... 260/29.6 R; 260/29.6 T; 260/29.6 RW
[58] Field of Search ..................... 260/29.6 R, 29.6 T, 260/29.6 RW

[56] References Cited

U.S. PATENT DOCUMENTS

| | | | |
|---|---|---|---|
| 2,831,833 | 4/1958 | Aycock et al. | 260/29.6 HN |
| 2,881,155 | 4/1959 | Hankins | 260/33.4 R |
| 2,881,171 | 4/1959 | Hankins | 260/69 R |
| 2,980,652 | 8/1961 | Melamed et al. | 260/2 R |
| 3,024,246 | 3/1962 | Goodman | 8/129 |
| 3,194,792 | 7/1965 | Emmons et al. | 260/33.6 R |
| 3,300,429 | 1/1967 | Glavis et al. | 260/29.6 RW |
| 3,369,008 | 2/1968 | Hurwitz | 260/79.7 |
| 3,973,946 | 8/1976 | Wah Wat | 71/92 |

OTHER PUBLICATIONS

Chemical Abstracts Reprint of the Introduction to the Subject Index to vol. 56, 1962, p. 91n.

*Primary Examiner*—Maurice J. Welsh
*Attorney, Agent, or Firm*—Russell L. Brewer; Barry Moyerman

[57] ABSTRACT

Improved wet adhesion properties of water-based paints and coating compositions are obtained by incorporating into the polymeric resin emulsion systems employed in the formulation of such paints or coating compositions a monomeric compound having a terminal ureido group at one end thereof and a vinyl terminal group at the opposite end. Such incorporated monomeric compounds correspond to the general formula

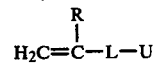

wherein R is H or CH₃, U designates a cyclic or acyclic ureido or thioureido group and L designates a selected linking structure. In the simplest of such monomeric compounds, L is —CH₂—, as specifically represented by allyl urea. In other representative compounds the linking group L may be a polymethylene group -$(CH_2)_n$—or the chain may contain one or more oxy (ether), amino, amido or carbonyl groups, provided that any carbonyl group (CO) present is not directly attached to U or to an ethylenic carbon atom nor is such ethylenic carbon directly attached to a nitrogen atom. Among preferred monomeric compounds imparting such improved wet adhesion are: N-Beta-allylaminoethyl ethylene urea, allyloxy-N-B-(1-ethylene ureido) ethyl acetamide, and allyl ester of N-ethyl-B-(1-ethylene ureido)-N-methyl carbamate. The polymer resin in the emulsion is one formed from one or more ethylenically unsaturated monomer compounds, such as acrylates and methacrylates, vinyl esters, vinyl chloride, mono- or di-ethylenic hydrocarbons; or copolymers, interpolymers or blends of these.

19 Claims, No Drawings

WET ADHESION EMULSIONS OF POLYMER RESINS SYSTEMS EMPLOYED IN WATER-BASED PAINT AND COATING COMPOSITIONS COMPRISING AS A COMPONENT THEREOF MONOMER CONTAINING AN ETHYLENIC DOUBLE BOND AND A UREIDO GROUP POLYMERIZED THEREIN

CROSS REFERENCE TO RELATED APPLICATION

The present application is a continuation-in-part of our application Ser. No. 709,677 filed July 29, 1976 now U.S. Pat. No. 4,111,877 which issued September 5, 1978. Novel monomeric compounds useful in enhancing wet adhesion and syntheses of such compounds are disclosed and claimed in copending application Serial No. 883,554 having a filing date of March 6, 1978, and entitled "Monomeric Compounds Having Vinyl and Ureido Terminal Groups."

BACKGROUND OF THE INVENTION

1. Field of the Invention

This invention relates generally to resin polymer emulsions used in formulation of water-based paints and coating compositions and is concerned particularly with improving the useful properties, more particularly the wet adhesion properties, of such paints and coating compositions. Such improvements are brought about by incorporation into the polymer resin emulsion certain monomeric compounds, as hereinafter described, which have at one end thereof a terminal ureido group and at the opposite terminal end, an unsaturated ethylenic group.

2. Prior Art

In U.S. Pat. No. 3,300,429 there are disclosed emulsions for water-based paints and coating compositions comprising addition polymers of (1) vinyl esters, (2) acrylic acid esters, and (3) mono- and di-ethylenically unsaturated hydrocarbons, stated to impart improved adhesion properties, including wet adhesion. The disclosed compositions of the patent comprise (1) the said water-insoluble addition polymer together with (2) a low molecular weight water-soluble ammonium salt of a copolymer of an alpha-beta unsaturated acid, said water insoluble addition polymer (1) or said soluble copolymer (2) having copolymerized therein a monomer having a cyclic or acyclic ureido group. A number of such ureido compounds are listed in the patent, and a wide variety of uses are indicated for the described compositions.

Various polymerizable compounds containing a terminal ureido group are disclosed in the prior art for a wide variety of different uses. Thus, in U.S. Pat. Nos. 2,881,155 and 2,881,171 there are disclosed cyclic ureido compounds terminated at the opposite end in an acrylic or methacrylic acid group. In U.S. Pat. No. 3,369,008, polymerization of N-(cyclic ureido-alkyl) crotonamides is disclosed, stated to be useful in adhesives, coating and textile finishing compositions. U.S. Pat. Nos. 2,980,652 and 3,194,792 disclose cyclic ureido compounds terminated at the opposite end by the residue of an unsaturated dicarboxylic acid. The ureido compounds of U.S. Pat. No. 3,024,246 terminate at the opposite end in an acrylamido group, and are stated to be useful as textile softening agents.

In our copending application Ser. No. 709,677 there are described novel cyclic ureido monomers terminating at the opposite end in the residue of an allyl or methallyl ester of a carboxylic acid

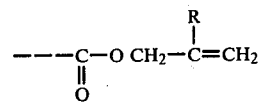

The compounds of said copending application, in contrast to the known cyclic ureido derivatives of the prior art, are characterized in that the carbonyl group in the chain linking the amino nitrogen of the N-amino alkyl urea to the terminal ethylene group is not directly attached to an ethylenic carbon atom.

In copending U.S. patent application, Ser. No. 709,916 filed July 29, 1976, now Pat. No. 4,104,220 the synthesis of novel allyl succinamic ureido compounds is described. These compounds as well as those described in the companion copending application Ser. No. 709,677 are shown to be particularly useful as functional comonomers for imparting improved wet adhesion properties to emulsion systems containing vinyl ester polymers, employed in paints and coating compositions.

SUMMARY OF THE INVENTION

It has now been found that the monomeric ureido compounds previously disclosed in our copending application Ser. No. 709,677 for improving the wet adhesion properties of waterbased paints comprising polymer emulsion systems containing vinyl ester polymers are also effective in improving the wet adhesion properties of such compositions employiing emulsions of other resin polymers, such as those containing acrylate and/or methacrylate esters. It has also been found that such enhancement of wet adhesion can be effected with other selected acyclic and cyclic ureido compounds including not only the new synthesized compounds disclosed in our companion copending application U.S. Ser. No. 883,554 and having a filing date of March 6, 1978 discussed previously, but also by use of certain relatively simple ethylenically unsaturated urea compounds, such as allyl urea.

Accordingly, the present invention is directed to polymer emulsion systems for incorporation in formulations for water-based paints and coating compositions, which emulsions contain, in addition to the usual polymer resin, a monomeric ureido compound corresponding to the formula

wherein R is H or CH$_3$, U designates a cyclic or acyclic ureido or thioureido group and L designates a selected linking chain connecting a ureido nitrogen to the vinylic

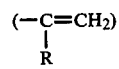

terminal group at the opposite end of the chain. The linking chain L may be a single methylene group —CH$_2$— or a polymethylene chain or such chain may contain one or more oxy (ether), amino, amido or carbonyl groups, provided that any carbonyl group (CO)

present is not directly attached to U or to an ethylenic carbon atom nor is an ethylenic carbon directly attached to a nitrogen atom. The ureido terminal group U may be acyclic corresponding to the structure

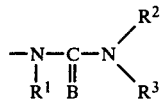 (a)

in which B is an oxygen or sulfur atom, and $R^1$, $R^2$ and $R^3$ each separately is hydrogen, alkyl, aryl, hydroxyalkyl or alkoxyalkyl or $R^2$ and $R^3$ may form a cyclic structure by being part of a piperidine, pyrrolidine or morpholine structure; or the ureido group may be cyclic, corresponding to the structure

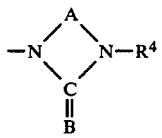 (b)

wherein B is as above defined, $R^4$ is hydrogen, alkyl, aryl, hydroxyalkyl or alkoxyalkyl, and A is an alkylene group of 2 to 3 carbon atoms, such as —CH$_2$CH$_2$—, —CH$_2$—CH$_2$—CH$_2$— or

—CH$_2$—CH(CH$_3$)—.

DESCRIPTION OF PREFERRED EMBODIMENTS

Compounds corresponding to formula I above, in their simplest form, are those in which the linking chain L is a —CH$_2$— group as in

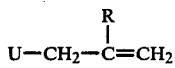 (II)

A simple example of such compounds is allyl urea of the formula

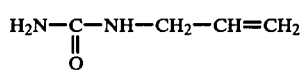 (IIa)

The useful compounds described in our copending application Ser. No. 709,677 contain as the linking chain L the group

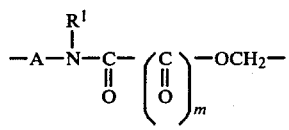 (III)

wherein m is zero or one. Illustrative specific compounds corresponding to the above are

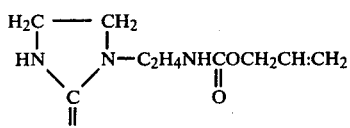 (IIIa)

and

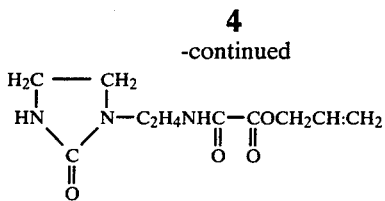 (IIIb)

and

Other related specific compounds containing the linking group III above and analogs thereof include those in which R is CH$_3$ and those in which

is replaced by oxygen, respectively as in

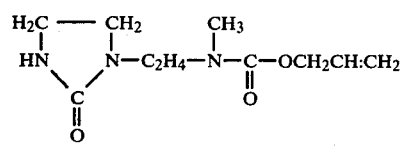 (IIIc)

and

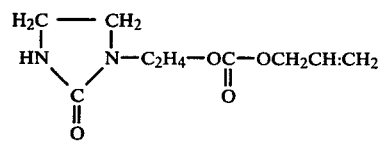 (IIId)

and

Compounds of the type IIIa and IIIb may be synthesized by the methods described in our copending application Ser. No. 709,677; respectively by (a) reaction of 2-aminoethyl ethyleneurea with diallyl carbonate or with allyl chloroformate and (b) by reaction of the 2-aminoethyl ethyleneurea with diallyl oxalate.

Among further types of compounds useful in practice of the invention are those corresponding to the general formula

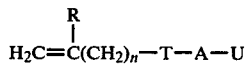 (IV)

wherein n is an integer from 1 to 9, T is oxygen or

and the other designations being as hereinbefore defined. A specific compound corresponding to the above formula IV are illustrated by

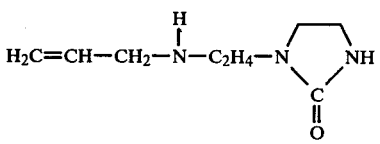 (IVa)

Also useful in practice of the invention are compounds represented by the general formula

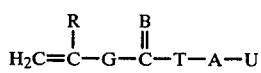 (V)

wherein

G is CH$_2$NR$^1$ — or CH$_2$O,

T is oxygen or

and the other symbols are as above defined. Specific examples of such compounds are those corresponding to the formulae

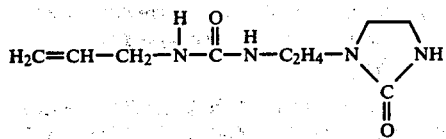
(Va)

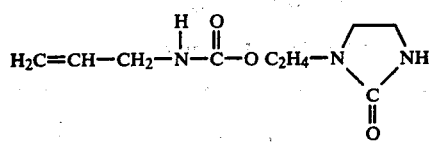
(Vb)

A further type of useful compound is represented by the general formula

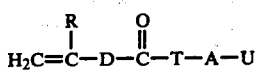
(VI)

wherein D is $-(CH_2)_n-$ or $-CH_2-T-(CH_2)_n-$.
Particular examples of such compounds are those represented by the formulae:

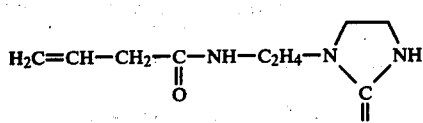
(VIa)

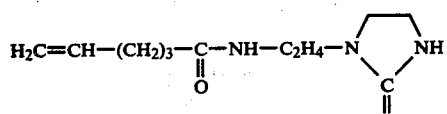
(VIb)

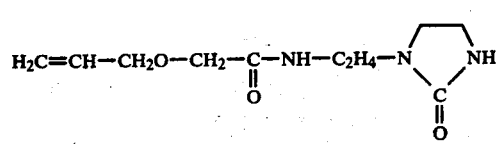
(VIc)

A further group of useful compounds is represented by the general formula

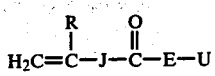
(VII)

wherein E represents an alkylene group of 1 to 10 carbon atoms and J is $-CH_2 O-$, $-CH_2 NR^1-$ or an oxygen atom. Illustrative examples of such compounds include those represented by the formulae

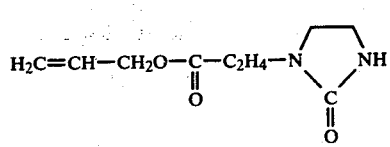
(VIIa)

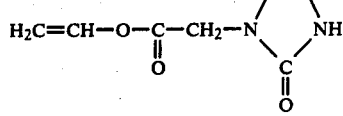
(VIIb)

Another group of useful compounds is that represented by the general formula

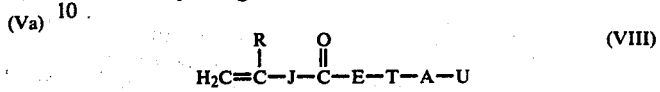
(VIII)

Illustrative examples of such compounds are

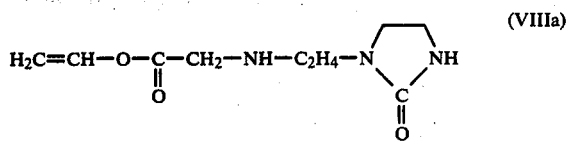
(VIIIa)

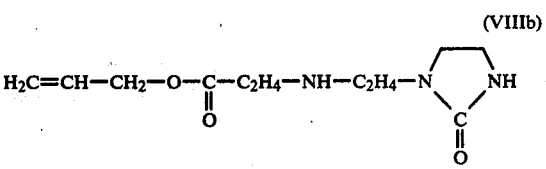
(VIIIb)

A further group of such compounds is that represented by the general formula

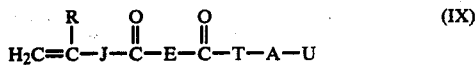
(IX)

A specific example of compounds coming within this group is that represented by the formula

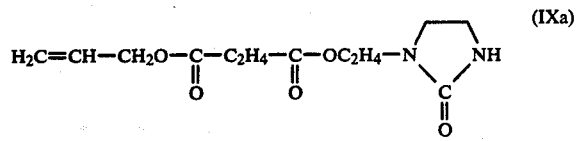
(IXa)

SYNTHESIS OF HCl SALT N-β-(ALLYLAMINO) ETHYL ETHYLENE UREA (FORMULA IVa)

To a reaction vessel containing 285.5 parts by weight of allylamine, there were added 148.04 parts of N-(β-chloroethyl)-N,N' ethylene urea and 750 parts distilled water. A slight exotherm was observed (temperature rise about 16° C.).

Heating was commenced with stirring, and an initial reflux temperature of 87.5° C. was observed. The reactants were permitted to reflux overnight, after which the contents were transferred to a concentrating vessel and heated at about 75° C. to remove water and excess allyl amine.

A mass of yellow waxy material was obtained. This product was taken up in absolute ethanol (350 parts product per 237 parts alcohol and to the resulting hot mixture there was added 630 parts by weight of ethyl acetate and the mixture set aside to cool slowly. Crystals of the hydrochloride salt of compound IVA were filtered off from the cooled mixture and dried in a vacuum oven at room temperature.

Actual yield obtained was 85.11% of theory. The crystalline product had a melting point of 151.5°–152.5° C.

| ELEMENTAL ANALYSIS | | | |
|---|---|---|---|
|  | C | H | N |
| Actual % | 45.95 | 7.99 | 19.94 |
| Theor. % | 46.74 | 7.78 | 20.44 |

Instead of reacting the chloroethyl urea compound with the allylamine, the same product can be obtained by reacting the 2-amino ethyl ethylene urea with allyl halide. If one employs as reactant with the ureido amine, the isomeric 1-halo-2-methyl-2-propene compound, corresponding compounds are obtained terminating in the

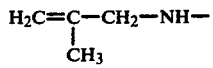

group.

PREPARATION OF ALLYL (B-1-ETHYLENEUREIDO) ETHYL CARBONATE (FORMULA IIId)

In a reaction vessel there were mixed

|  | pbw |
|---|---|
| N-β-hydroxyethyl-N,N'-ethylene urea | 130 |
| Methylene chloride | 1325.5 |
| Triethylamine | 126.31 |

To the resulting mixture there was added dropwise 150.6 parts allyl chloroformate while maintaining the temperature at 10°–15° C. The addition took about 1.5 hours.

The mixture began to reflux at about 45° C., and was continued overnight. It was then filtered with suction and the filtrate containing the product was concentrated under vacuum. The last traces of solvent were removed by vacuum pumping overnight with heating to 50° C.; and then dried. Actual yield was 88.7% of theory.

| ELEMENTAL ANALYSIS | | | |
|---|---|---|---|
|  | C | H | N |
| % theory | 50.49 | 7.51 | 13.08 |
| % actual | 51.54 | 6.53 | 12.63 |

SYNTHESIS OF n-[B-1-ETHYLENEUREIDO] ETHYL ALLYLOXYACETAMIDE (FORMULA VIc)

The reactants comprised:

|  | pbw |
|---|---|
| N-(β-aminoethyl)-N,N'-ethylene urea | 71 |
| Allyl allyloxyacetate | 86.23 |
| Acetonitrile | 157.14 |

These were added one after another to a reaction vessel and the mixture stirred for about 2 hours at room temperature. A TLC (thin layer chromotography) plate was run on the mixture which indicated that some product was formed.

The reaction was maintained at 50° C. for about 17 hours. The TLC plate was again run on the mixture which indicated further product formation.

The reaction was heated for an additional three hours, then cooled and filtered to remove the precipitated impurities. The filtrate was stripped of acetonitrile and allyl alcohol by rotary evaporation. A clear yellow oil remained which solidified on standing at room temperature. The obtained solid material was recrystallized from ethanol/ethyl ether and had a melting point of 73°–74° C. The actual yield of recrystallized product was 45.16% of theory.

PRODUCTION OF ALLYL N-METHYL-N-β-(1-ETHYLENE UREIDO) ETHYL CARBAMATE (FORMULA IIIc)

In a reaction vessel there were mixed

|  | pbw |
|---|---|
| N-(B-Methylaminoethyl)-N,N' ethylene urea | 18 |
| Methylene chloride | 99.4 |
| Sodium hydroxide (30% solution in water) | 143. |

To this stirred solution there was added dropwise with cooling 12 parts of allyl chloroformate, keeping the temperature between 15°–20° C.

The reaction mixture was then stirred at room temperature for about an hour and let stand to permit the product to separate into layers. The bottom layer comprising the methylene chloride solution was dried over anhydrous magnesium sulfate. Following filtration to remove the magnesium sulfate, the methylene chloride solvent was stripped off at about 30° C. under vacuum. The product was obtained at 87.27% of theoretical yield.

It was confirmed by TLC that there was only one component in the reaction product and the structure was confirmed by NMR (nuclear magnetic resomance spectroscopy).

| ELEMENTAL ANALYSIS | | | |
|---|---|---|---|
|  | C | H | N |
| Theoretical % | 52.88 | 7.48 | 18.5 |
| Actual % | 51.61 | 7.78 | 18.14 |

The compounds of the invention may be incorporated in emulsion systems containing acrylic, vinyl ester or other pigmented or non-pigmented aqueous emulsion systems useful in paints and coatings in the manner described in the aforesaid copending applications. The following specific example illustrates the polymerization of a ureido compound of the type described to form an interpolymer within a commercial interpolymer system comprising vinyl acetate, vinyl chloride, ethylene and maleic acid.

EXAMPLE 1

To a pressure vessel, there was charged:

|  | parts by weight (p.b.w.) |
|---|---|
| Vinyl acetate | 4540 |
| a) Triton X-301 (20%) | 1040 |
| b) Igepal CO-730 | 416 |
| c) Siponate DS-10 | 208 |
| Sodium vinyl sulfonate (25%) | 98 |
| Potassium persulfate | 300 |

-continued

|  | parts by weight (p.b.w.) |
|---|---|
| Ferrous salt | 1.5 |
| Water | 8170 |

The agitated vessel contents initially showed a pH of 3.2.

The kettle contents were purged with N₂ and agitated at 150 rpm. Upon heating to 46° C., the charge was pressurized to 900 psi (63.28 kg/cm²) with ethylene. Polymerization was initiated with a 2.0% Discolite solution and there were simultaneously added to the kettle the following compositions in 5 delays.

In the first delay, the initiator was introduced over a period of eight hours and was composed of:

|  | Delay 1 | p.b.w. |
|---|---|---|
| (d) | Discolite | 200 |
|  | water | 4600 |
|  | NH₄OH (28%) | 200 |

The second and third delays were introduced during a three hour period. These comprised:

| Delay 2 | Delay 3 |
|---|---|
| 4540 parts vinyl acetate | 9090 parts vinyl chloride |

The fourth and fith delays were introduced during a four hour period. These comprised:

| Delay 4 | p.b.w. | Delay 5 | p.b.w. |
|---|---|---|---|
| Maleic acid (29% sol) | 664 | ureido cmpd.III(a) | 363 |
| sodium vinyl sulfonate | 293 | water | 1816 |
| water | 2227 |  |  |

(a) Anionic surfactant-sodium salt of an alkaryl polyether sulfate.

(b) Nonionic surfactant; nonylphenoxy ethanol comprising 75% ethylene oxide.

(c) Anionic surfactant; purified dodecyl benzene sodium sulfonate.

(d) Sodium formaldehyde sulfoxylate.

The polymerization temperature was maintained at 50° C. with a jacket temperature of 23°–50° C. The kettle pressure was maintained at 960 psi (67.5 kg/cm²) throughout the delays. At the end of the delays, the vinyl acetate free monomer content was less than 0.5%. The final emulsion had a solids content of 53.4% and the final pH was adjusted to 5.0. This emulsion when incorporated into a semi-gloss paint had outstanding wet adhesion.

An example for preparation of another emulsion system comprising a copolymer of vinyl acetate with ethylene and maleic acid is as follows.

EXAMPLE 2

There was charged to a pressure vessel

|  | parts by weight |
|---|---|
| Vinyl acetate | 1,907 |
| (e) Igepal CO 887 | 1,218 |
| (f) Igepal CO 630 | 426 |
| Sodium vinyl sulfonate (25%) | 158 |
| Polysodium vinyl sulfonate (25%) | 171 |

-continued

|  | parts by weight |
|---|---|
| Potassium persulfate | 80 |
| Fe⁺⁺ | 0.3 |
| Water | 18,160 |

The stirred mixture had an initial pH of 3.2.

The kettle contents were stirred at 150 rpm, purged with nitrogen, and then pressurized to 570 psi (=40 kg/cm²) while heating to 50° C. Polymerization was initiated with a 50% solution of Discolite and there were added to the kettle simultaneously over a four hour period, four delays as follows:

| Delay 1 |  | Delay 2 |  |
|---|---|---|---|
|  | pbw |  | pbw |
| Vinyl acetate | 19,749 | Maleic anhyd. | 115 |
| Triallyl cyanurate | 8,898 | Sodium vinyl sulfonate (25%) | 173 |
|  |  | Pot. persulfate | 58 |
|  |  | Water | 922 |
| Delay 3 |  | Delay 4 |  |
| Discolite | 250 | Ureido compound III(a) | 363 |
| NH₄OH (28%) | 150 | Water | 4631 |
| Water | 5,000 |  |  |

(e) Nonyl phenoxypoly (ethyleneoxy) ethanol comprising 86 % ethylene oxide.

(f) Nonyl phenoxypoly (ethyleneoxy) ethanol comprising 65 % ethylene oxide.

The polymerization temperature was maintained at 50° C. with a jacket temperature of 43° C. and ethylene pressure of 570 psi (=30 kg/cm²) during the course of the delays. At the end of the delays, and when the vinyl acetate free monomer content was less than 0.5%, the emulsion was cooled to ambient temperature and transferred to a degasser. The emulsion contained 50% solids and imparted outstanding wet adhesion to semi-gloss paints.

A further example of an emulsion system comprising a copolymer of vinyl acetate and butyl acrylate made up for a semigloss paint which showed particularly good wet adhesion properties with addition of selected ureido compounds, was formulated as follows:

EXAMPLE 3

Into a jacketed reaction vessel there was charged

|  | pbw |
|---|---|
| Hydroxyethyl cellulose | 0.45 |
| Alkyl phenoxy poly(oxyethylene)ethanols | 13.7 |
| Ferrous salt | (trace) |
| De-ionized water | 380 |

The vessel and contents were purged with nitrogen while heated at 65° C. and stirred. There were then added to the vessel at delayed intervals the following three mixtures

| Mixture 1 | pbw |
|---|---|
| Vinyl acetate | 415.2 |
| Butyl acrylate | 67.5 |
| *Pluronics | 15.6 |
| t-Butyl peroxide (70%) | 0.7 |

*Pluronics are non-ionic block polymers comprising polyalkylene derivatives of propylene glycol terminating in hydroxyl.

| Mixture 2 | pbw |
|---|---|
| Sodium formaldehyde bisulfite | 0.2 |

|  | |
|---|---|
| Sodium benzoate | 0.6 |
| De-ionized water | 8.2 |
| Mixture 3 | pbw |
| Ureido compound III(a) | 2.4 |
| De-ionized water | 72.0 |

The first and third mixtures were added over a two hour period while the second was added during a fifteen minute period. The polymerization mixture was maintained at 65° C. After addition of the second mixture was completd, there was further added a solution of 0.6 parts of sodium formaldehyde bisulfite in 18.1 parts de-ionized water until polymerization was completed. The emulsion was then cooled to ambient temperature. It had a pH of 5.2 and contained 55.4% solids. Addition of a pigment dispersion to the emulsion provided a semigloss paint having outstanding wet adhesion.

An example of an all acrylic emulsion to which improved wet adhesion properties is conferred by incorporation of the selected ureido compounds is formulated as follows.

EXAMPLE 4

To a reaction vessel there were added:

|  | pbw |
|---|---|
| Igepal CO 887 | 61 |
| Igepal CO 630 | 31.3 |
| $Fe^{++}$ | trace |
| Water | 935.8 |

The contents of the vessel were stirred at 120 rpm and heated to 65° C. under a nitrogen purge. There were then added to the reaction vessel over a two hour period, three delays, as follows:

| Delay 1 | pbw |
|---|---|
| Ethyl acrylate | 480 |
| Methyl Methacrylate | 320 |
| t-butyl hydroperoxide (70%) | 1.4 |
| Delay 2 | |
| Sodium formaldehyde sulfoxylate | 1.5 |
| Sodium benzoate | 1.1 |
| Deionized water | 48.5 |
| Delay 3 | |
| Ureido compound III(a) | 8.0 |
| Deionized water | 92 |

The polymerization temperature was maintained at 65°–66° C. with a cooling jacket temperature of 60° C. At the end of the delays, there was added to the emulsion 2.0 parts of sodium formaldehyde sulfoxylate and 1 part of t-butyl hydroperoxide mixed with 10 parts water. The obtained emulsion had 44.4% solids and a pH of 5.1.

The foregoing emulsion put into a standard semigloss paint formulation, passed the cut film wet adhesion test described below.

The cut film test employed is a standard procedure for testing wet adhesion to a surface of semi-gloss paint as set out in Federal Specification TT-P-001511, paragraph 4.3.9 (GSA-FSS). In this test a panel is painted with an alkyd enamel of specified composition and permitted to dry under specified conditions. The test paint is then applied over the alkyd surface and dried. A cut is then made longitudinally through the center of the test film and the panel scrubbed under water at a specified rate of brush travel. To pass this test, there must be no loss of adhesion between the test paint and the alkyd undercoat and no wearing through to the undercoat in fewer than 5,000 cycles.

In the recut test, a second cut is made perpendicular to the first on the test film. The board is subject to an additional 1000 cycles of under water brushing.

In the "floating board" the composition to be tested is applied over a dry glossy alkyd-painted plane board surface and dried. A one-inch section of the surface is scored by cross-hatching with parallel cuts vertical and horizontal 1/10-⅛ inch apart. An adhesive tape is applied to the dry scored surface and the relative amounts of the surface film peeled off by the adhesive observed. The board is again similarly scored and then floated face down on a water bath to wet the scored surface and the adhesive tape procedure repeated, again observing the amount of painted surface removed.

A representative number of ureido compounds were each incorporated into an emulsion system for testing of wet adhesion properties. The systems tested contained 0.75% of the ureido compound. Other amido compounds were also included in these tests as well as a control free of additive.

The results of the tests are shown in Tables 1 and 2 below, respectively, on the cut film and floating board tests.

The emulsion systems employed in all of the tests reported in Tables 1 and 2 were similarly prepared except for the particular ureido or amido compound employed to determine its properties for conferring improved wet adhesion to the paint composition into which the emulsion was incorporated.

The emulsion systems were prepared by mixing in a reaction vessel, a seed emulsion composed of:

|  | pbw |
|---|---|
| (g) FLEXBOND® 325 (55% solids) | 91. |
| Natrosal 25.0 LR (hydroxy-ethyl cellulose) | 0.89 |
| $Fe^{++}$ | trace |
| Deionized water | 539. |

(g) A copolymer emulsion prepared from 86 parts vinyl acetate, 14 parts butyl acrylate, stabilized with hydroxyethyl cellulose.

The reactants were agitated at 200 RPM and heated to 65° C. while purging with nitrogen. There were simultaneously delayed to the emulsion seed over a 2 hour period, the following:

|  | pbw |
|---|---|
| Vinyl acetate | 868. |
| n-Butyl acrylate | 97. |
| Igepal CO 887 | 15. |
| Igepal CO 630 | 10.5 |
| Pluronic F 68 | 15.5 |
| Pluronic L 64 | 15.5 |
| t-Butyl hydroperoxide (70%) | 1.4 |

Followed by a solution composed of

| Uredio or amide compound being tested | 0.75% by weight of monomers |
|---|---|
| Deionized water | 200 parts |

The polymerization temperature was maintained at 65° C. using an activator solution consisting of

| | pbw |
|---|---|
| Discolite PEA | 0.4 |
| Sodium benzoate | 1.1 |
| Deionized water | 16.4 |

The vinyl acetate free monomer content was kept between 3-5% throughout the polymerization with a jacket temperature between 53°-65° C. At the end of the delays, and when the vinyl-acetate-free monomer content was below 0.5%, the emulsion was cooled. The final pH was 5.1 and solids content were 55.6%.

TABLE 1

| | Cut Film | |
|---|---|---|
| Test Compound | 1st cut 5000 cycles | Recut 1000 cycles |
| N-allyl urea | Pass | Pass |
| Allyl carbamate | Fails after 250 | Fails at 340 |
| B-Allyloxy propionamide | Fails at 100 | Fails at 239 |
| Compound of Formula IIIc | Pass | Pass |
| Compound of Formula IIId | Fail | Pass |
| N-carbamyl maleamic acid | Fail | — |
| Compound of formula IVa | Pass | Pass |
| Compound of formula IVc | Pass | Pass |
| 3-butenamide | Fail | — |
| N-carboallyloxy urea | Fail | — |
| N-carboallyloxy ethylene urea | Fails | — |
| N-(allyloxyacetyl)ethylene urea | Fails | — |
| Control (no additive) | Completely stripped | Fails at 100 cycles |

TABLE 2

| | FLOATING BOARD | |
|---|---|---|
| Test compound | % Removal wet | % Removal dry |
| N-allyl urea | 0 | 0 |
| Allyl carbamate | 26 | 4 |
| B-Allyloxy propionamide | 98 | 0 |
| Compound of Formula IIIc | 1 | 0 |
| Compound of Formula IIId | 98 | 7 |
| N-carbamyl maleamic acid | 82 | 1 |
| Compound of Formula IVa | 8 | 10 |
| Compound of Formula VIc | 16 | 4 |
| 3-buteneamide | 5 | 1 |
| Control | 100 | 80 |

While the compound of Formula III(d) failed to pass the 5000 cycle wet adhesion test, it did pass the 1000 cycle recut test, and therefore showed significant improvement over the control which failed both of these tests.

The novel ureido monomers of the invention can be incorporated into aqueous paint or coating formulations by interpolymerization in emulsions comprising acrylates or methacrylates, or in emulsions comprising vinyl ester systems which may contain one or more other unsaturated monomers. Thus, such systems may comprise vinyl acetate alone or in admixture with one or more monomers from among ethylene, vinyl chloride, maleic acid, and alkyl esters of acrylic, methacrylic and maleic acids. Such emulsion systems generally comprise, in addition to the polymerizable monomer or monomers, free radical initiators and emulsifying, stabilizing, and surface active agents. Preferably, the activator comprises a redox system, typically made up of a peroxide or persulfate catalyst and a reducing component, such as an alkali metal formaldehyde bisulfite or sulfoxylate. The principal emulsifying agent is preferably one of the nonionic type and may also include surface agents of the anionic type.

The novel ureido compounds of the invention, added to water-based flat exterior paints also impart improved resistance to blistering.

What is claimed is:

1. Aqueous emulsions of polymer resin systems employed in water-based paint and coating compositions, comprising as a component thereof conferring enhanced wet adhesion properties, a reactable monomer corresponding to the structural formula

wherein R is hydrogen or methyl, U designates a cyclic or acylic ureido or thioureido group and L designates $CH_2$ or a linking chain containing in said chain at least one moiety from the group consisting of oxygen, amido, amino, and carbonyl, provided that any carbonyl group present is not directly attached to U or to an ethylenic carbon atom nor is an ethylenic carbon directly attached to a nitrogen atom, said reactable monomer being polymerized into said polymer resin system.

2. Aqueous emulsions as defined in claim 1 wherein said polymer resin is a vinyl ester polymer.

3. Aqueous emulsions as defined in claim 2 wherein L is $CH_2$.

4. Aqueous emulsions as defined in claim 2 wherein said reactable monomer is that corresponding to the formula

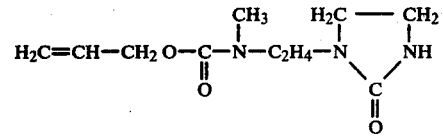

5. Aqueous emulsions as defined in claim 2 wherein said reactable monomer is that corresponding to the formula

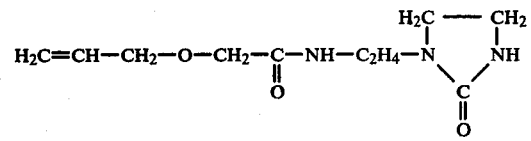

6. The aqueous emulsion of claim 5 wherein said polymer resin comprises vinyl acetate and an acrylic ester.

7. Aqueous emulsions as defined in claim 2 wherein said reactable monomer is allyl urea.

8. Aqueous emulsions as defined in claim 1 wherein said polymer resin is a polymer of an acrylate or methacrylate ester.

9. Aqueous emulsions as defined in claim 8 wherein said reactable monomer is that corresponding to the formula

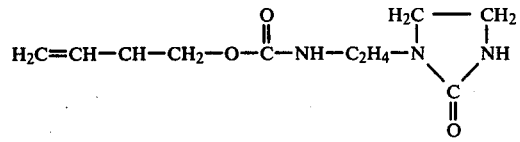

10. Aqueous emulsions as defined in claim 1 wherein U is a cyclic ureido group corresponding to the structure

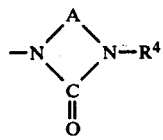

wherein R⁴ is hydrogen, alkyl, aryl, hydroxyalkyl or alkoxyalkyl, and A is an alkylene group of 2 to 3 carbon atoms selected from the group consisting of —CH₂—CH₂——CH₂—CH₂—CH₂—and —H₂C—CH(CH₃).

11. Aqueous emulsions as defined in claim 10 wherein R⁴ is hydrogen and L is a linking chain selected from the group consisting of:

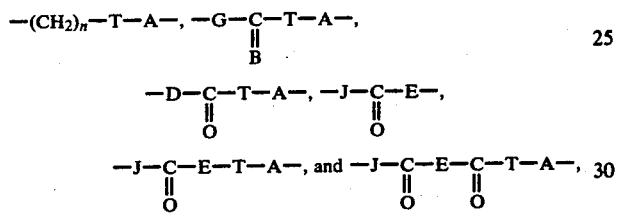

wherein n is an integer from 1 to 9, T is oxygen or

$R^1$ is hydrogen, alkyl, aryl, hydroxyalkyl, or alkoxyalkyl; A is an alkylene group of 2 to 3 carbon atoms, G is —CH₂NR¹— or —CH₂O—, B is oxygen or sulfur; D is —(CH₂)ₙ— or —CH₂—T—(CH₂)ₙ; E is an alkylene group of one to ten carbon atoms, and J is —CH₂O—, —CH₂NR¹— or an oxygen atom.

12. Aqueous emulsions as defined in claim 11 wherein said polymer resin system comprises a vinyl ester polymer.

13. Aqueous emulsions as defined in claim 11 wherein said polymer resin system comprises the polymerization product of vinyl acetate in admixture with at least one polymerizable monomer from the group consisting of ethylene, vinyl chloride, alkyl esters of acrylic acid, alkyl esters of methacrylic acid, and maleic acid.

14. Aqueous emulsions as defined in claim 11 wherein said polymer resin system comprises the copolymer of vinyl acetate and butyl acrylate.

15. Water-based paints having incorporated therein a polymer resin emulsion as defined in claim 4.

16. Water-based paints having incorporated therein a polymer resin emulsion as defined in claim 5.

17. Water-based paints having incorporated therein a polymer resin emulsion as defined in claim 6.

18. Water-based paints having incorporated therein a polymer resin emulsion as defined in claim 7.

19. Water-based paints having incorporated therein a polymer resin emulsion as defined in claim 9.

* * * * *

Disclaimer

4,151,142.—*Frederick L. Herman*, Allentown and *Dale Davis Dixon*, Kutztown, Pa. WET ADHESION EMULSIONS OF POLYMER RESINS SYSTEMS EMPLOYED IN WATER-BASED PAINT AND COATING COMPOSITIONS COMPRISING AS A COMPONENT THEREOF MONOMER CONTAINING AN ETHYLENIC DOUBLE BOND AND A UREIDO GROUP POLYMERIZED THEREIN. Patent dated Apr. 24, 1979. Disclaimer filed Mar. 16, 1981, _ by the assigneeProducts and Chemicals, Inc.

Hereby enters this disclaimer to claims 1, 2 and 11–14 of said patent.
[*Official Gazette May 19, 1981.*]